(12) United States Patent
Ouchi

(10) Patent No.: US 6,402,738 B1
(45) Date of Patent: Jun. 11, 2002

(54) WIRE CONNECTION STRUCTURE FOR ENDOSCOPE

(75) Inventor: Teruo Ouchi, Saitama-ken (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/494,547

(22) Filed: Jan. 31, 2000

(30) Foreign Application Priority Data

Feb. 4, 1999 (JP) ............................................ 11-027023

(51) Int. Cl.[7] .............................................. A61B 17/00
(52) U.S. Cl. .......................................... 606/1; 600/146
(58) Field of Search ................................ 600/146, 149; 606/205, 1

(56) References Cited

U.S. PATENT DOCUMENTS 3,892,228 A * 7/1975 Mitsui ........................... 128/4
5,127,916 A * 7/1992 Spencer et al. ............. 606/185
5,435,296 A * 7/1995 Vivenzio et al. ............ 600/146
5,454,378 A * 10/1995 Palmer et al. ............... 128/751
5,517,755 A * 5/1996 Wright ......................... 29/843
6,074,408 A * 6/2000 Freeman ..................... 606/205
6,198,974 B1 * 3/2001 Webster, Jr. ................ 607/122

* cited by examiner

*Primary Examiner*—Linda C. M. Dvorak
*Assistant Examiner*—Jocelyn Ram
(74) *Attorney, Agent, or Firm*—Greenblum & Bernstein, P.L.C.

(57) ABSTRACT

In a connection structure for connecting a stranded operation wire and a connection member of an endoscope, an end of the stranded operation wire is formed to be an integrally fixed portion where a plurality of strands constituting the stranded operation wire are fixed to each other, and a hole, in which at least the integrally fixed portion of the stranded operation wire is inserted, is formed. The connection member is plastically deformed with the stranded operation wire inserted therein such that the connection member and the stranded operation wire located in said hole are engaged with each other.

5 Claims, 6 Drawing Sheets

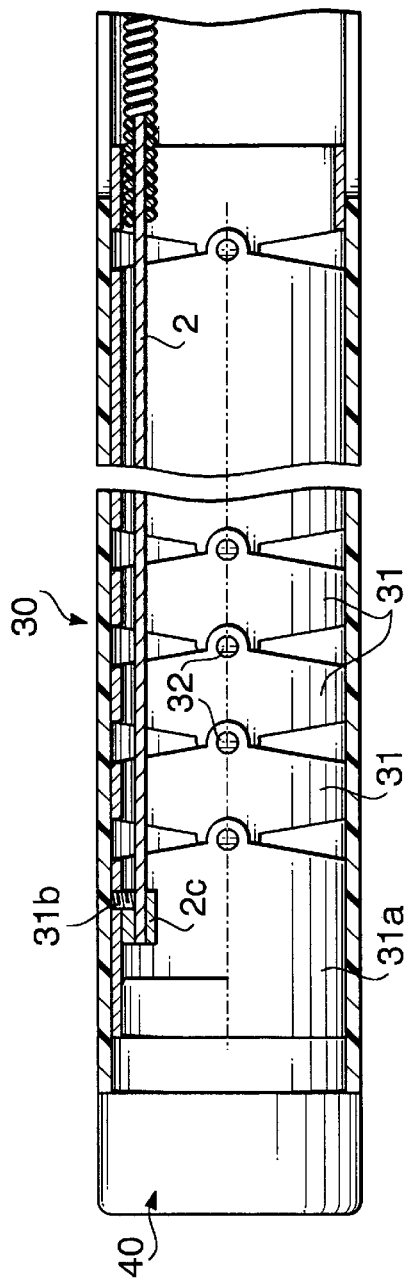
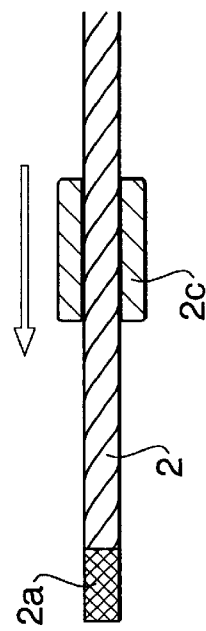
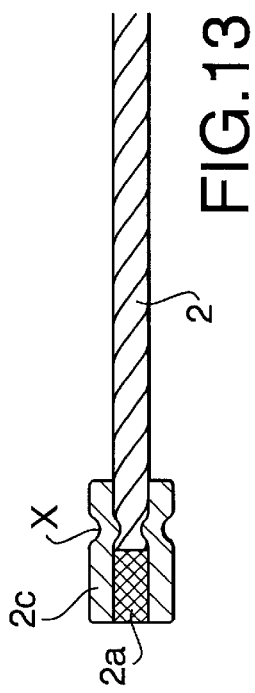
FIG. 11
FIG. 12
FIG. 13

WIRE CONNECTION STRUCTURE FOR ENDOSCOPE

BACKGROUND OF THE INVENTION

The present invention relates to a wire connection structure for connecting an operation wire to a member, (to which the operation wire is connected,) for an endoscope.

As an operation wire for an endoscope, a stranded wire is generally used. The stranded wire is a wire formed by twisting a plurality of thin wires so that it does not have a bending property. When such a stranded wire is connected to another member, for example, an end of the stranded wire is inserted into a hole formed in the member, with which the stranded wire is connected, and then, the end of the stranded wire is silver brazed or soldered thereto.

When the stranded wire is silver brazed, the portions of the stranded wire and the connected member should be heated up to 600° C. In order to heat the portion to be brazed, a small burner or the like is used as a heating tool. Due to difference of heat capacity, the portion of the stranded wire which is not inserted in the connected member tends to be heated easily in comparison with the portion of the wire inserted in the connected member. Therefore, to the portion of the stranded wire that is to be brazed, the brazing silver is hardly applied, while, the portion of the stranded wire that is not brazed is heated and the brazing silver may be applied thereto. In such a case, the portion hardened by the brazing silver may be longer than a designed length, or the operation wire (i.e., the stranded wire) may be oxidized and the strength may be weakened.

If the stranded wire is to be soldered to the connected member, the fixing strength is inherently weak, and even a small amount of residual flux remains, the soldered portion may be broken off. Therefore, in this case, the flux should be completely cleaned, which is very troublesome.

SUMMARY OF THE INVENTION

It is therefore an object of the invention to provide an improved connection structure for connecting an operation wire with a member to be connected at stable strength with a simple and reliable process.

For the above object, according to the invention, there is provided a connection structure for connecting a stranded operation wire and a connection member of an endoscope, in which an end of the stranded operation wire is formed to be an integrally fixed portion where a plurality of strands constituting the stranded operation wire are fixed to each other, and a hole is formed on the connection member, at least the integrally fixed portion of the stranded operation wire being inserted in the hole, the connection member being plastically deformed such that the connection member and the stranded operation wire located in the hole being engaged with each other.

Since the tip of the stranded wire is integrally fixed, removal of the tip portion through the plastically deformed connection member is prevented. Accordingly, the operation wire can be firmly secured to the connection member.

In one example, a portion of the wire inserted in the hole includes the integrally fixed portion and a stranded wire portion that is not integrally fixed, a position where the connection member is plastically deformed corresponding to the stranded wire portion next to the integrally deformed portion.

In this case, the deformed portion of the connection member is well pushed into the stranded wire portion.

Alternatively or optionally, a position where the connection member is plastically deformed corresponds to the integrally deformed portion.

Since the integrally fixed portion hardly deforms and therefore it prevents the removal of the operation wire through the deformed portion of the connection member.

The stranded operation wire may be an operation wire of a treatment accessory of the endoscope. Alternatively, the stranded operation wire may be a operation wire for moving a bendable portion of a main body of the endoscope.

In particular, an engaging protrusion having a through hole is provided on an inner surface of the bendable portion. The operation wire is provided with an engaging member, and the engaging member is inserted through the through hole formed on the protrusion from a distal end side of the endoscope to a proximal end side.

With this structure, the wire and the connection member are firmly connected, and the engaging member is prevented from passing through the hole formed on the engaging protrusion. Therefore, when the wire is drawn at the proximal end of the endoscope, the bendable portion is bent due to the drawing force of the operation wire.

BRIEF DESCRIPTION OF THE ACCOMPANYING DRAWINGS

Figure 8:
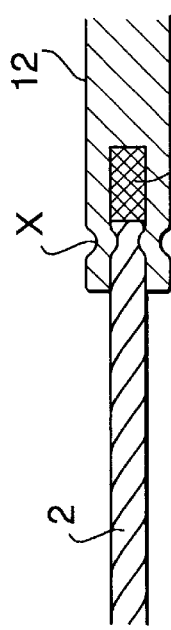
Figure 9:
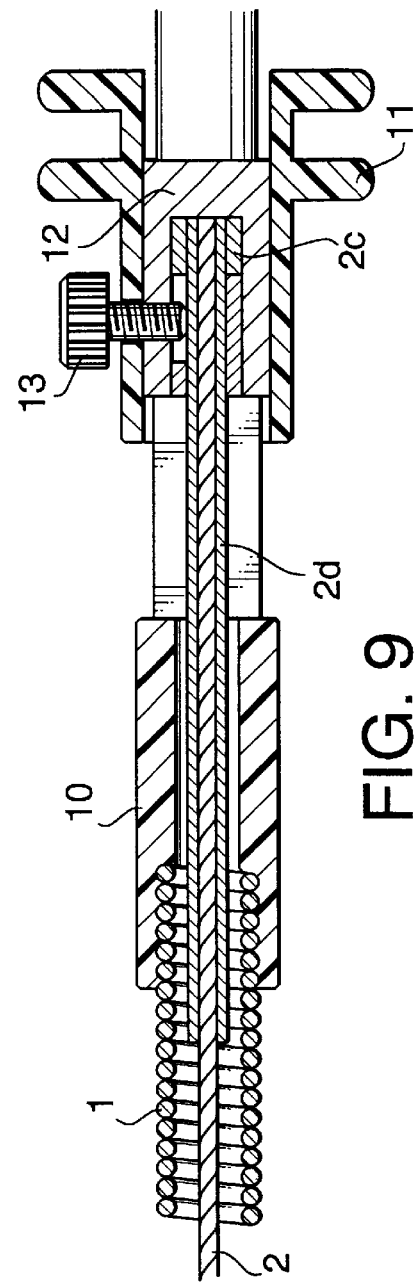
Figure 10:
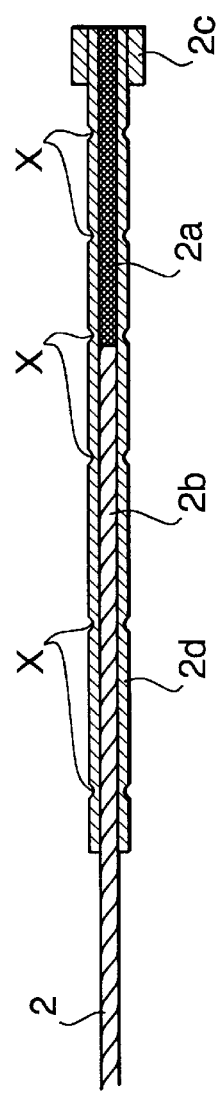

FIG. 8 a partially cross-sectional side view of a tip end portion of a treatment accessory of an endoscope according to a third embodiment;

FIG. 9 a partially cross-sectional side view of a tip end portion of a treatment accessory of an endoscope according to a fourth embodiment;

FIG. 10 is a cross-sectional side view of a proximal end portion of the operation wire according to the fourth embodiment;

FIG. 11 is a cross-sectional side view of a bent portion of an endoscope according to a fifth embodiment of the invention;

FIG. 12 is a cross-sectional view for illustrating a procedure of producing an operation wire to be used in the endoscope shown in FIG. 11; and FIG. 13 is a cross-sectional view for illustrating a procedure of producing an operation wire to be used in the endoscope.

DESCRIPTION OF THE EMBODIMENTS

Hereinafter, embodiments of the present invention will be described with reference to the accompanying drawings.

Figure 2:
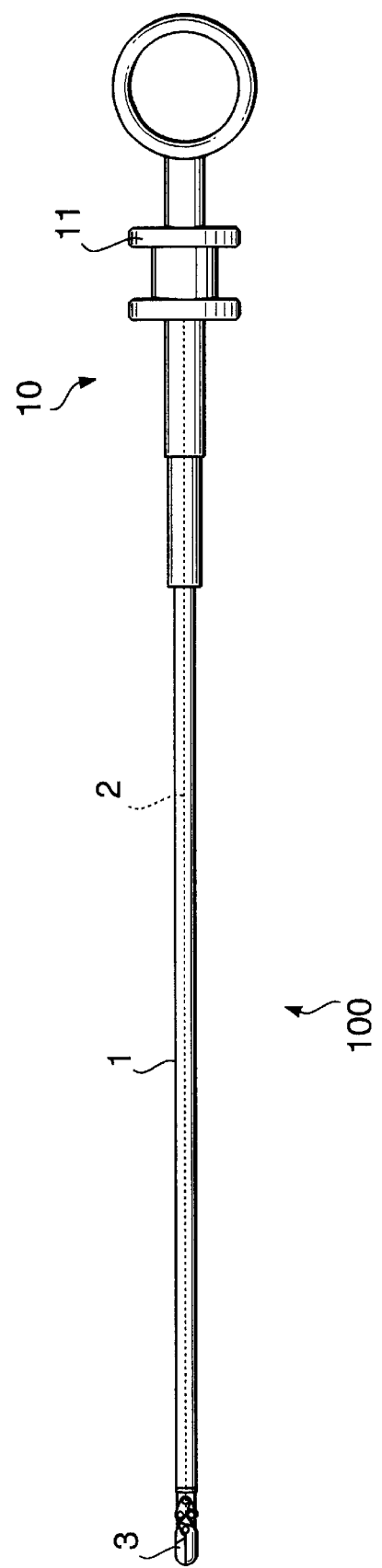
FIG. 2 is a side view of the treatment accessory according to the first embodiment.

FIG. 2 is a side view of a biopsy forceps 100 which is one of the treatment accessories for an endoscope. The biopsy forceps is to be inserted in a forceps channel of an endoscope (not shown). Specifically, the biopsy forceps shown in FIG. 2 has a flexible sheath 1 that is to be inserted in the forceps channel of the endoscope. An operation wire 2 is provided inside the sheath 1 over an entire length thereof. The operation wire 2 is slidable with respect to the sheath 1 along an axis thereof. To a proximal end of the sheath 1, a manipulation unit 10 is connected. The manipulation unit 10 has a slider 11. By moving the slider 11 with respect to the sheath 1 in the axial direction, a pair of cups 3 mounted at a tip end of the sheath 1 is driven, by the operation wire 2, to open and close.

Figure 1:
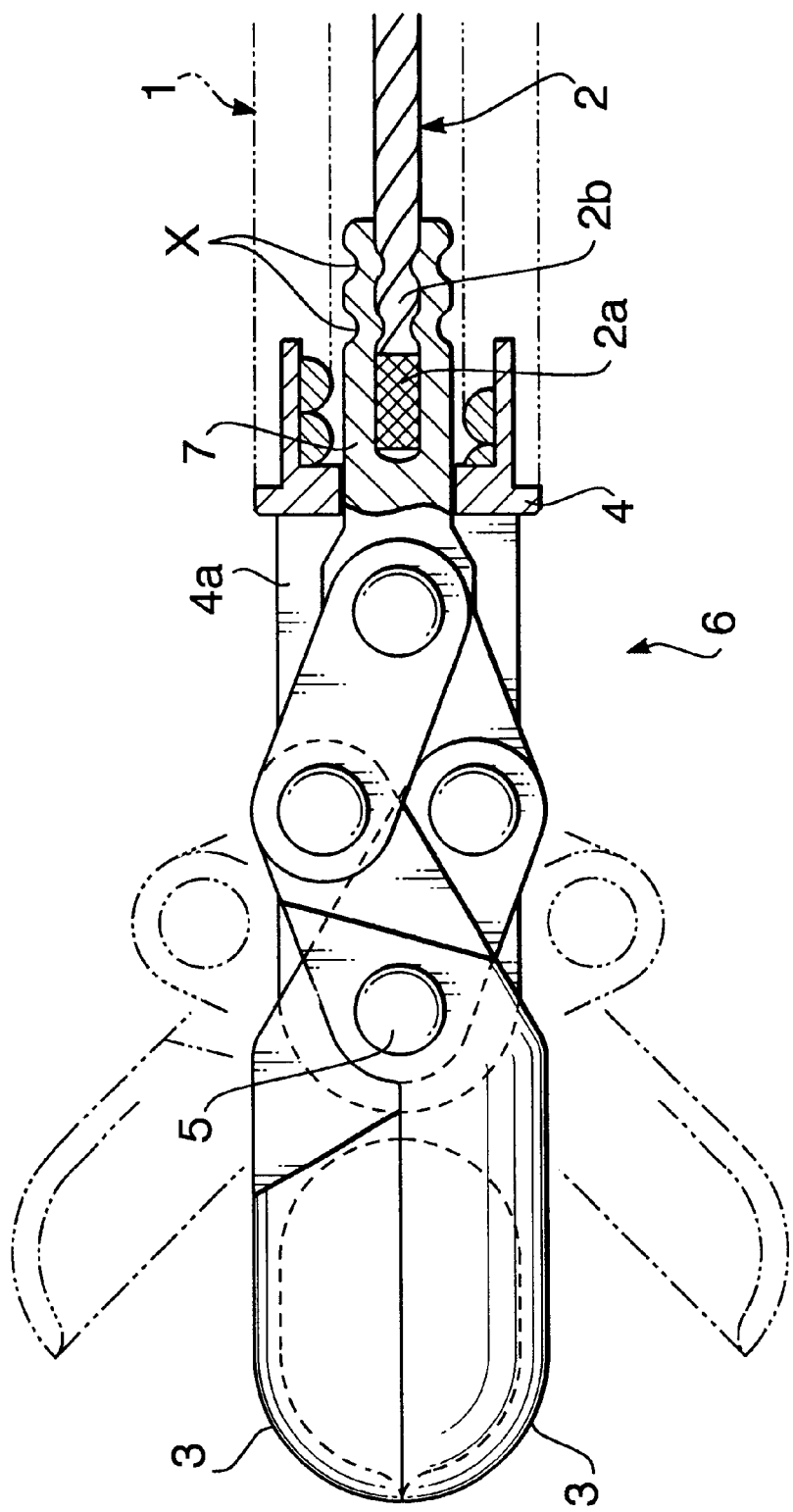
FIG. 1 is a partially cross-sectional side view of a tip portion of a treatment accessory of an endoscope according to a first embodiment of the invention.

FIG. 1 shows a tip end portion of the biopsy forceps 100. At a distal end of the sheath 1, a supporting member 4 is fixedly secured. On the supporting member 4, a slotted portion 4a, where a pair of slots are provided at opposite positions with respect to a central axis of the supporting member 4, is formed. At the tip portion of the slotted portion 4a, a pin 5 is provided. The pin 5 extends in a direction of the diameter of the slotted portion 4a, and a pair of cups 3 are openably (i.e., rotatably) supported by the pin 5.

Inside the slotted portion 4a, a link mechanism 6 is provided to open and close the cups 3. At the proximal end side of the link mechanism 6, a connection member 7 made of stainless steel is secured. As shown in FIG. 1, the tip of the operation wire 2 is connected to the connection member 7.

Figure 3:
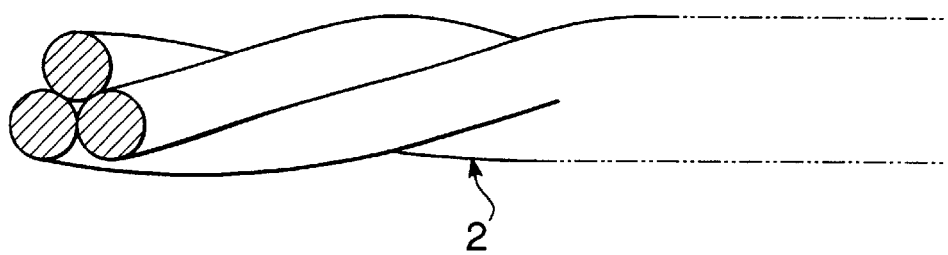
FIG. 3 is a side view including a front view of a 1×3 stranded wire (i.e., a stranded wire consisting of three thin wires)
Figure 4:
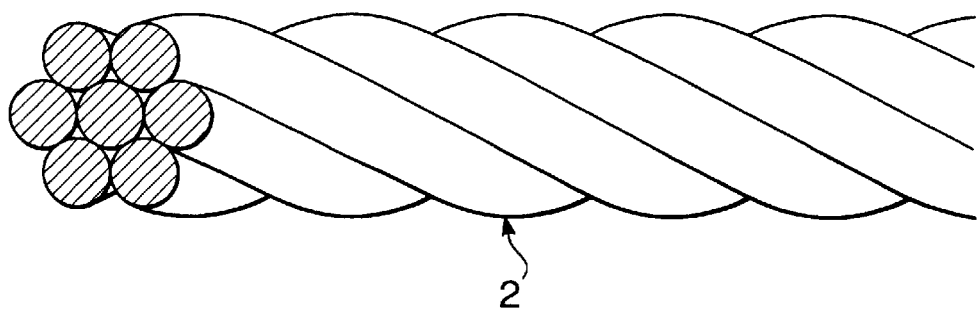
FIG. 4 is a side view including a front view of a 1×7 stranded wire (i.e., a stranded wire consisting of seven thin wires)
Figure 5:
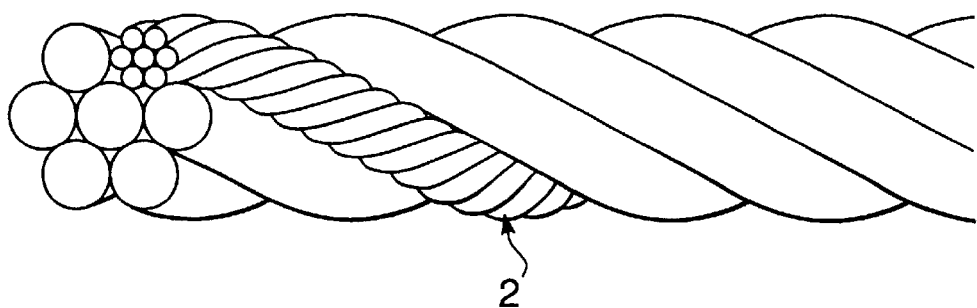
FIG. 5 is aside view including a front view of a 7×7 stranded wire (i.e., a stranded wire consisting of seven stranded wires, each of which consists of a seven thin wires)

The operation wire 2 is a stranded wire composed of a plurality of thin wires twisted with each other. FIGS. 3–5 show examples of the stranded wires for the biopsy forceps 100. FIG. 3 shows a 1×3 stranded wire, which consists of three single thin wires; FIG. 4 shows a 1×7 stranded wire which consists of seven single thin wires; and FIG. 5 shows 7×7 stranded wire which consists of seven stranded wires, each of which is a 1×7 stranded wire. It should be noted that the wires shown in FIGS. 3–5 are examples of the stranded wire, and any other wires of a similar type can be used.

At the tip portion 2a of the stranded wire 2, the wires (constituting the stranded wire are integrally secured with each other by silver brazing, soldering, plasma welding, or the like.) The tip portion will be referred to as an integrally fixed portion, hereinafter.

The connection member 7 has a hole at the proximal end side portion thereof, and the integrally fixed portion 2a of the operation wire 2 is inserted in the hole. The outside shape of the connection member 7 is formed to be cylindrical at the end side portion where the hole is formed. The cylindrical portion is deformed plastically, at two axially different positions (which will be referred to as swaged portions X), so as to internally protrude and push into the wire 2, thereby the wire 2 being fixedly secured to the connection member 7.

With the above structure, since the integrally fixed portion 2a of the wire 2 is unable to pass through the narrow part of the swaged portions X, the connection member 7 and the wire 2 are connected very strongly.

Figure 6:
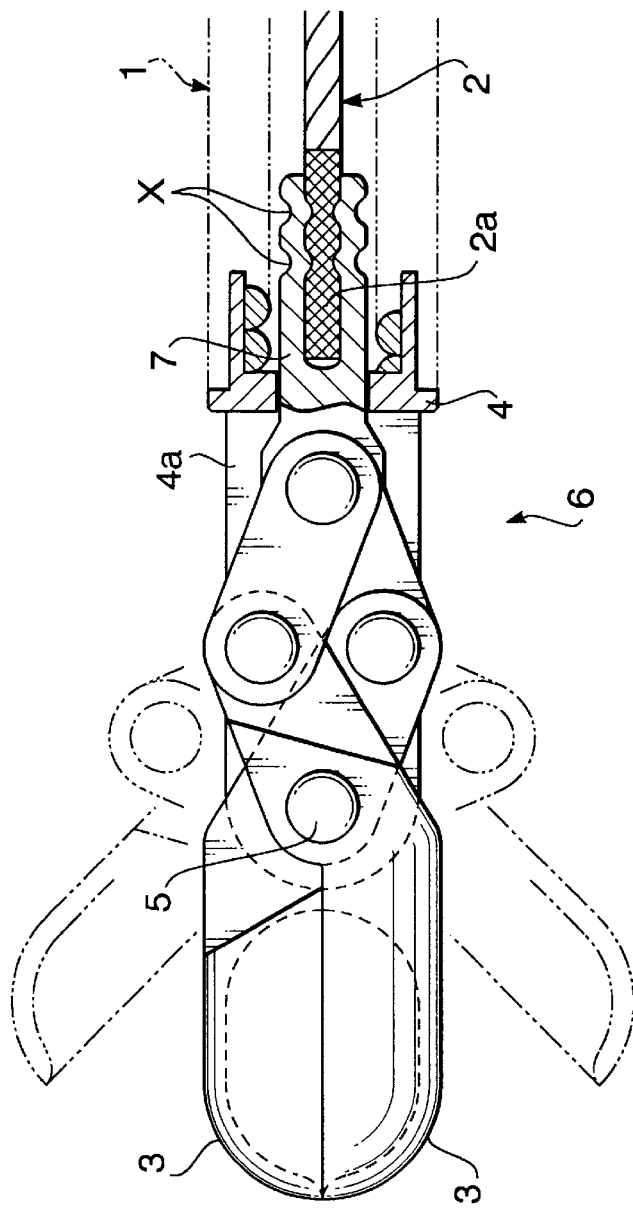
FIG. 6 is a partially cross-sectional side view of a tip end portion of a treatment accessory of an endoscope according to a second embodiment.

In this embodiment, as shown in FIG. 1, the integrally fixed portion 2a is located on the cup side with respect to the swaged portions X, and the portion of the stranded wire which is not integrally fixed is located at the swaged portions X. With this structure, the swaged portions X are well pushed into the stranded wire 2, and further, the integrally fixed portion 2a is well prevented from passing through the swaged portions X. It should be noted that, the integrally fixed portion 2a may be located at the swaged portions X, as in a second embodiment shown in FIG. 6. In this case, the swaged portions X are pushed in the wire 2, and therefore, the wire 2 and the connection member 7 are connected strongly as well.

Figure 7:
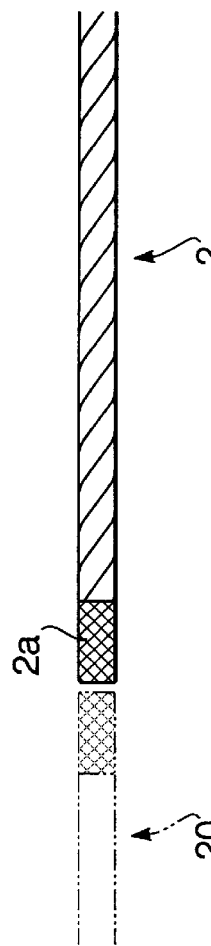
FIG. 7 is a side view illustrating a procedure for producing the operation wire.

FIG. 7 illustrates a method of forming the integrally fixed portion 2a. Firstly, an intermediate portion of a wire 2 is silver brazed (alternatively, soldered or plasma-welded) to form an elongated integrally fixed portion. Then, the integrally fixed elongated portion is cut so that an appropriate integrally fixed portion 2a remains. With this method, two integrally fixed portions can be formed simultaneously on both sides of a position where the wire 2 is cut.

In accordance with the above method, the integrally fixed portion 2a can be formed to have an appropriate length with the least heat deterioration to the wire 2. The above-described fixing process is followed by a cleaning process for cleansing the wire 2 of the flux.

In the above-described embodiment, the invention is applied to the tip of the operation wire 2 for the biopsy forceps. FIG. 8 shows the connection structure according to a third embodiment. As shown in FIG. 8, the invention is also applicable to the proximal end of the wire 2. Specifically, in FIG. 8, 12 denotes a connection member connected to a slider 11 of the manipulation section 10. As shown in FIG. 8, the swaged portion X may be a single portion. It should be noted that two or more swaged portions may be formed at the proximal end portion, and at the distal end portion, only a single swaged portion may also function.

FIG. 9 shows a structure for detachably fixing the wire 2 to the slider 11, according to a fourth embodiment of the invention.

FIG. 10 shows the structure of wire 2 and a stainless steel pipe 2d surrounding the wire 2, according to the fourth embodiment. As shown in FIG. 10, at an end of the pipe 2d, an engaging member 2c is secured with the silver brazing, soldering or plasma-welding. The engaging member 2c functions to prevent the wire 2 from detached from the slider 11 when the engaging member 2c is inserted in a hole formed on the connector 12 and a screw 13 is fastened (see FIG. 9). The wire 2 is inserted inside the pipe 2d, and the pipe 2d is swaged at four or five portions (which are referred to as swaged portions X) along the central axis thereof. In the embodiment shown in FIG. 10, the swaged portions X are formed both at the integrally fixed portion 2a and the stranded portion 2b, where the wires consisting of the stranded wire 2 are merely twisted but not integrally fixed with silver brazing or the like.

When the operation wire 2 constructed as above is inserted in the connector 12 and the screw 13 is fastened, the operation wire 2 can be firmly fixed with respect to the slider 11. By loosening the screw 13, the wire 2 can easily be detached from the slider 11.

Such a structure is effective not only for the biopsy forceps but also for any treatment accessory which is constituted such that a sheath and a manipulation section can be separated.

FIG. 11 shows a bendable portion 30 formed at a distal end portion of an endoscope according to a fifth embodiment of the invention. The bendable portion 30 is formed of a plurality of (e.g., 5–15) rings 31 which are connected with rivets so as to be rotatable to each other. To a ring 31a, which is located at the distal end of a main body 40 of the endoscope, an objective optical system is mounted.

On an inner surface of the ring 31a, an engaging protrusion 31b formed with a through hole is provided. As shown in FIG. 11, an operation wire 2 which is provided with an engaging member 2c is inserted through the through hole formed on the protrusion 31b from the distal end side of the endoscope to the proximal end side thereof. By drawing the operation wire 2 at an operation section connected to the proximal end of the insertion portion of the endoscope, the bendable portion 30 bends.

A process for fixedly securing the engaging member 2c at the tip of the wire 2 is similar to that in the above-described embodiments. That is, firstly, an integrally fixed portion 2a is formed at the tip of the operation wire (see FIG. 12). Then, the engaging member 2c having a hole that can be fitted on the wire 2 is inserted from an end opposite to the integrally fixed portion 2a, as shown in FIG. 12. Then, the engaging member 2c is swaged as shown in FIG. 13.

According to the present invention, an end of a stranded wire is formed to be the integrally fixed portion by silver brazing, soldering or plasma-welding, the end of the wire including the integrally fixed portion is inserted into a hole that is formed on a member to which the wire is connected, and then the member to which the wire is connected is swaged so that the member and the wire is fixedly secured. Since the tip of the stranded wire is integrally fixed, the tip of the wire does not pass through the member to which the wire is connected. Therefore, the wire and the member are secured fixedly with a relatively simple method.

The present disclosure relates to the subject matter contained in Japanese Patent Application No. HEI 11-027023, filed on Feb. 4, 1999, which is expressly incorporated herein by reference in its entirety.

What is claimed is:

1. A connection structure for a stranded operation wire adapted for use in an endoscope, comprising:

an integrally fixed portion where a plurality of strands constituting said stranded operation wire are fixed to each other, said integrally fixed portion being formed at an end of said stranded operation wire; and a connection member having a hole therein, at least said integrally fixed portion of said stranded operation wire extending into said hole, said connection member being plastically deformed such that said connection member and said stranded operation wire extending into said hole are engaged with each other.

2. The connection structure according to claim 1, wherein a portion of said wire inserted in said hole includes said integrally fixed portion and a stranded wire portion that is not integrally fixed, and wherein a position where said connection member is plastically deformed corresponds to the stranded wire portion next to said integrally fixed portion.

3. The connection structure according to claim 1, wherein a position where said connection member is plastically deformed corresponds to a stranded wire portion next to said integrally fixed portion.

4. The connection structure according to claim 1, wherein said stranded operation wire is an operation wire of a treatment accessory of the endoscope.

5. A connection structure for a stranded operation wire of an endoscope, comprising:

an integrally fixed portion where a plurality of strands constituting said stranded operation wire are fixed to each other, said integrally fixed portion being formed at an end of said stranded operation wire, said stranded operation wire comprising an operation wire for bending a bendable portion of the endoscope;

an engaging protrusion having a through hole provided on an inner surface of the bendable portion; and an engaging member provided on said stranded operation wire extending through the through hole formed on said engaging protrusion from a distal end side to a proximal end side of the endoscope, whereby said bendable portion of the endoscope is bendable by said stranded operation wire.

* * * * *